United States Patent [19]

Givner

[11] 4,208,187

[45] Jun. 17, 1980

[54] DIAGNOSTIC TEST

[75] Inventor: Morris L. Givner, Pierrefonds, Canada

[73] Assignee: American Home Products Corp., New York, N.Y.

[21] Appl. No.: 949,174

[22] Filed: Oct. 6, 1978

Related U.S. Application Data

[63] Continuation-in-part of Ser. No. 862,062, Dec. 19, 1977, Pat. No. 4,138,214.

[51] Int. Cl.$^2$ .................... G01N 33/16; B01D 31/00; G01N 21/04
[52] U.S. Cl. .................................. 23/230 B; 23/915; 23/917; 210/22 R; 210/23 F; 422/59; 422/69; 422/101; 424/12
[58] Field of Search ................. 23/230 B, 917; 424/12; 210/22 R, 23 F; 422/59, 69, 101

[56] References Cited

U.S. PATENT DOCUMENTS

| | | | |
|---|---|---|---|
| 3,485,751 | 12/1969 | Herrmann | 210/22 |
| 3,488,768 | 1/1970 | Rigopulos | 210/23 |
| 3,817,379 | 6/1974 | Zipilivan | 210/94 |
| 3,991,174 | 11/1976 | Grundman | 424/12 |
| 4,022,576 | 5/1977 | Parker | 23/230 B |
| 4,033,723 | 7/1977 | Givner | 424/12 X |
| 4,123,224 | 10/1978 | Givner | 424/12 X |
| 4,123,509 | 10/1978 | Banik | 210/22 R X |
| 4,123,510 | 10/1978 | Banik | 23/230 B X |

FOREIGN PATENT DOCUMENTS 126454 8/1967 Czechoslovakia .

OTHER PUBLICATIONS

B. Vierneisel, Zentr. Gynaekol., 83(48), 1915 (1961).
Chemical Abstracts, 62:8079b (1965).
F. Orlandi et al., Folia Endocrinol., 17(4), 505(1964).
M. L. Taymor et al., J. Endocrinol, 36, 417 (1966).
J. Vaitukaitis et al., J. Clin. Endocrinol., 33, 988(1971).
P. Franchimont et al., Proc. Int. Symp. Protein and Polypeptide Hormones, Excepta Med. Found., 1967, pp. 381, 383–387.
G. Fine et al., Amer. J. Clin. Pathol., 49, 171 (1968).
S. U. Lok et al., Asian J. of Med., 9, 319 (1973).
L. K. Curtiss et al., J. Virology, 14, 503 (1974).
L. Wide, Acta Endocrinol., Supp. vol. 70, 1962, pp. 68–74.
M. Killip et al., J. Clin Pathol., 61, 337 (1974).
H. Wagner, Acta Endocrin., Suppl. vol. 31, 1957, pp. 90–99.
M. J. Lyaght, ACS Meeting, Apr. 1–5, 1974, vol. 34, No. 1, Coating and Plastic Preprints of Papers, pp. 578–581.
Amicon Corp. Sci. System Div., Pre–Concentration and Deprotenization in the Clinical Laboratory, Pub. 434, May 1973, pp. 1–7.
T. Tamada et al., J. Clin. Endocrinol., 27, 379 (1967).
B. M. Hobson, J. Reprod. Fert., 12, 33 (1966).
Prognosticon 'All-in', Organon Flyer, product instructions, 4 pp.
Med. World News, McGraw-Hill, Feb. 1, 1974, p. 24.
P. Jame et al., Path–Biol., 19, 1115 (1971), English summary on p. 1119.
R. Plan et al., Ann. Biol. Clin (Paris) 19, 169–170 (1961).
Chemical Abstracts, 57:1220f (1962).
Edwards, Physiol. Effects of Immunity Against Reproductive Hormones, Cambridge Univ. Press, London, Clinical & Exptl. Immunoreproduction, vol. 3, 1976, pp. 23–32.

*Primary Examiner*—Sidney Marantz
*Attorney, Agent, or Firm*—Adley F. Mandel

[57] ABSTRACT

A simple, sensitive, reliable and safe method and device for detecting a polypeptide or glycoprotein antigen. The test involves concentration in the presence of polyvinylpyrrolidone by ultrafiltration of a sample of urine or serum from a subject; followed by determining the presence of said polypeptide or glycoprotein antigen or a particular subunit thereof in the concentrated sample.

20 Claims, 19 Drawing Figures

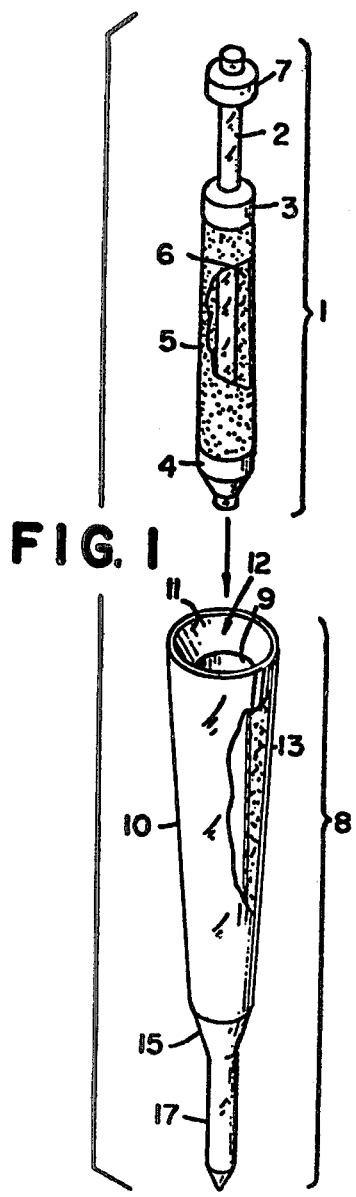
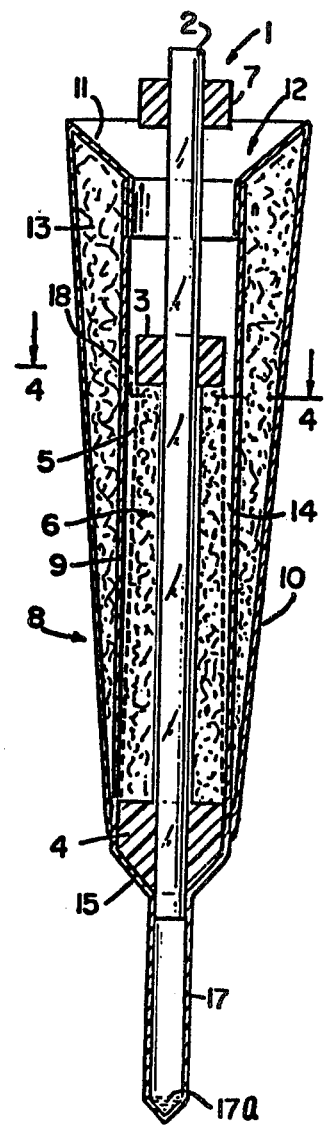
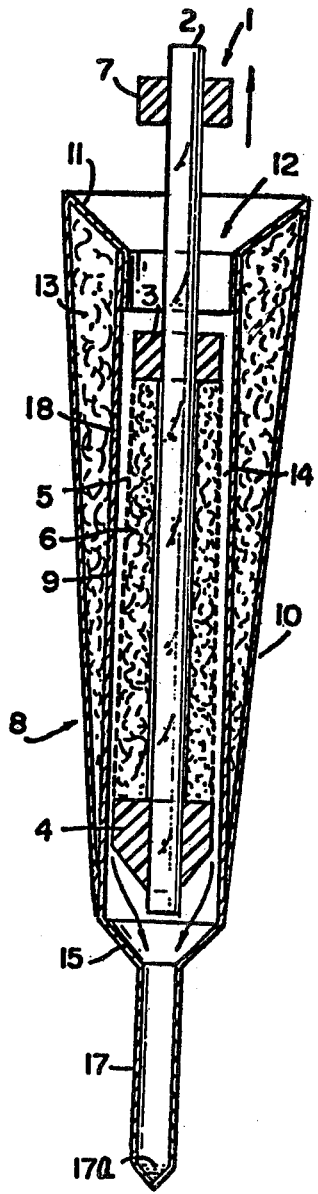
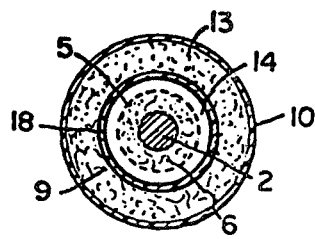
FIG. 1
FIG. 2
FIG. 3
FIG. 4

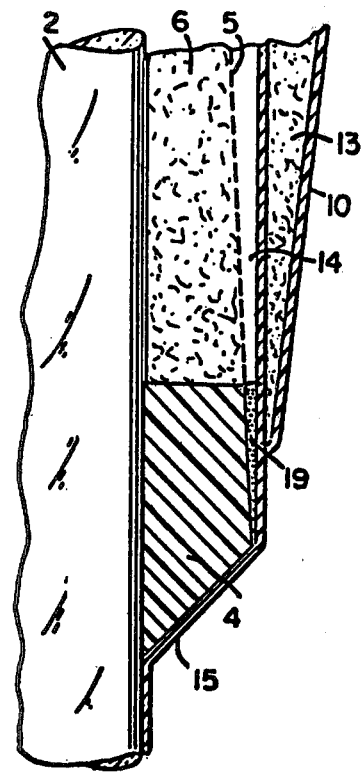
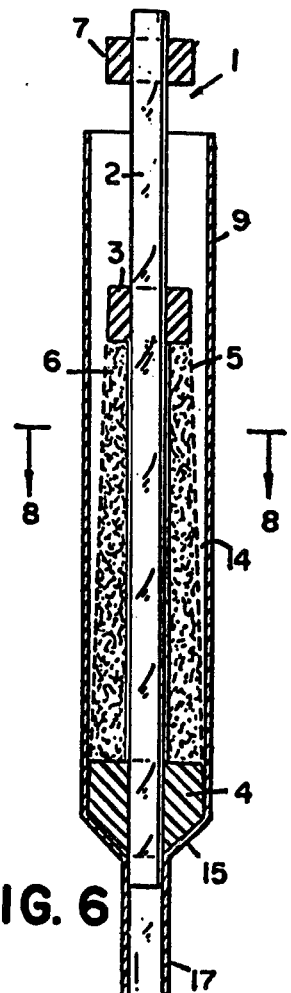
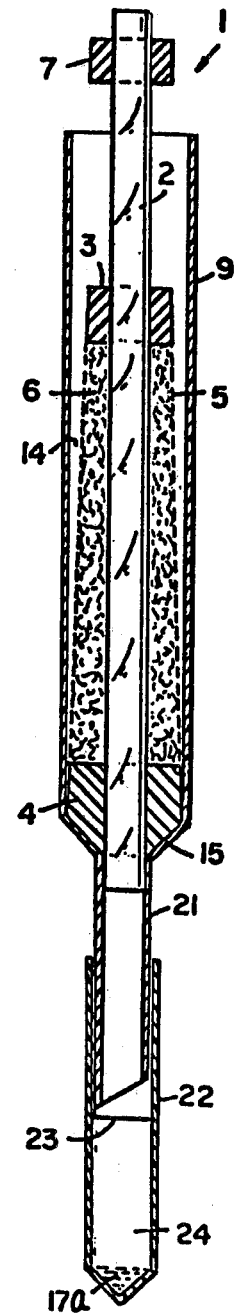
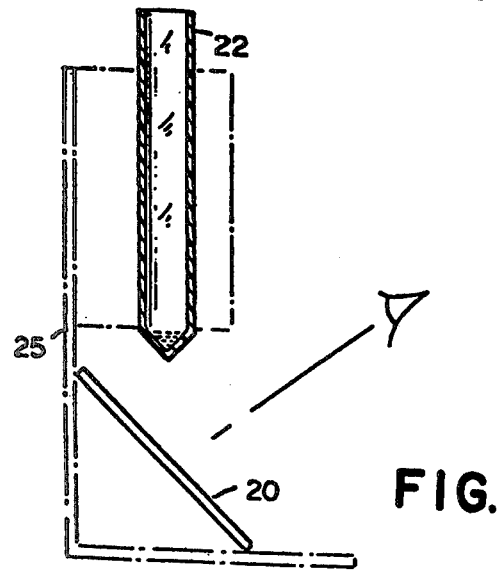
FIG. 5
FIG. 6
FIG. 9
FIG. 7

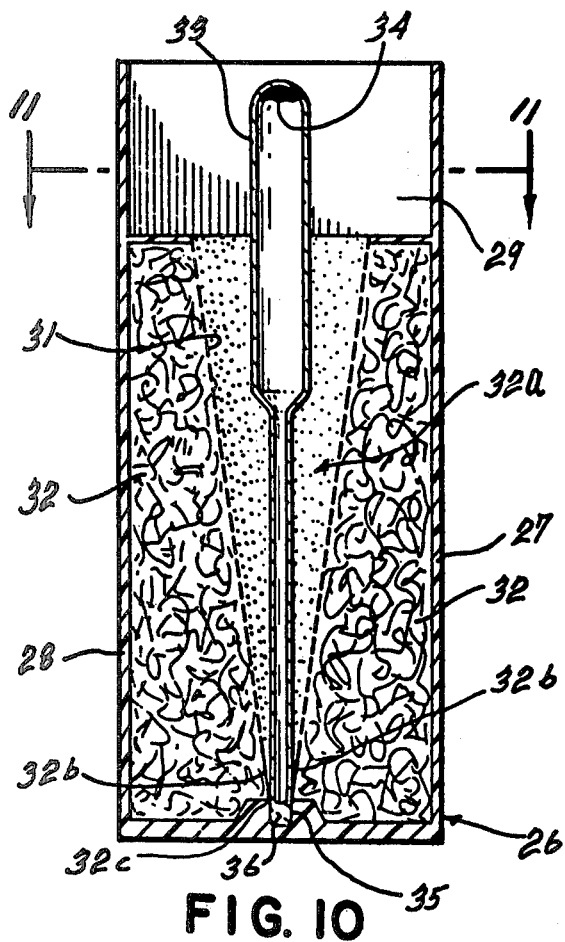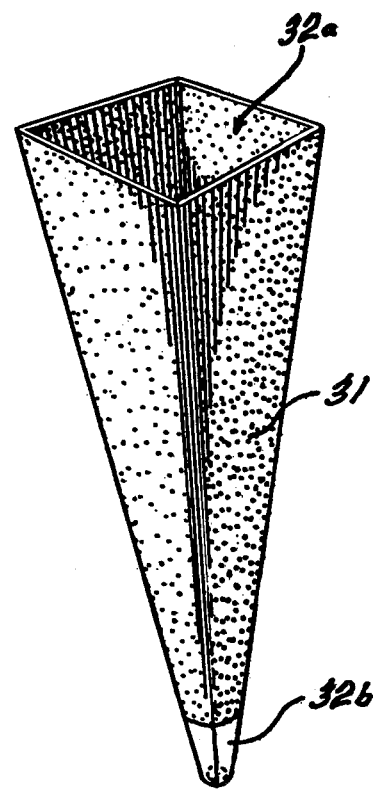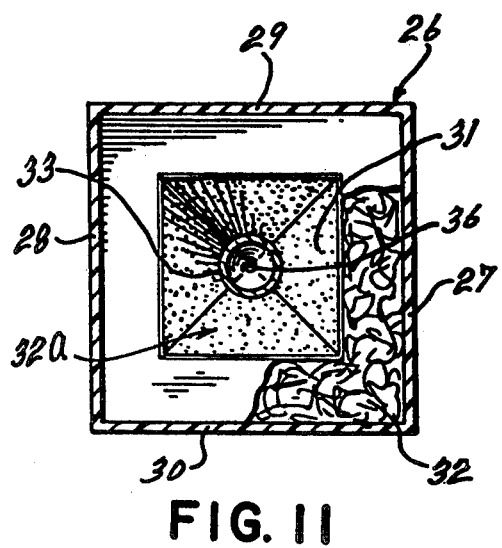

DIAGNOSTIC TEST

REFERENCE TO RELATED APPLICATIONS

This application is a continuation-in-part of co-pending application, Ser. No. 862,062, filed Dec. 19, 1977, now U.S. Pat. No. 4,138,214, issued Feb. 6, 1979.

BACKGROUND OF THE INVENTION (a) Field of the Invention

This invention relates to a method and device suitable for the detection of certain physiological conditions characterized by the presence of a polypeptide or glycoprotein antigen. More specifically, this invention concerns a simple and sensitive method and device for the detection of various placental and pituitary gonadotropins and hormones. The invention, in the main, is illustrated as a method and device for the detection of pregnancy in women; the method and device being especially useful for the detection of pregnancy in its very early stages.

(b) Prior Art

A simple, sensitive test for the early diagnosis of human pregnancy would be an important contribution to medicine and society. For instance, it would be advantageous in cases of unwanted pregnancies or in cases of habitual aborters who would benefit from early therapy. It would also be advantageous for the physician to have knowledge of an early pregnancy before prescribing a drug that may be teratogenic, or in those instances where a woman has unwittingly been exposed to a possibly teratogenic drug. Also, not to be overlooked, is the all important psychological factor for the woman to know for certain whether she is pregnant or not.

The most widely used pregnancy tests employed today are those based on the detection of human chorionic gonadotropin (HCG) in urine samples by immunological methods. These tests rely on the fact that HCG is the gonadotropin of pregnancy, being secreted by the chorionic tissue of the placenta in increasing amounts soon after the implantation therein of a fertilized ovum. [The peak secretion of HCG of more than 50,000 i.u. per a 24 hour collection of urine occurs between 56 and 84 days after the last menstrual period, E. H. Venning in "Text Book of Gynecologic Endocrinology", J. J. Gold, Ed., Harper and Row, New York, 1968, pp. 95–97]. These tests are generally reliable for detecting pregnancy after about the twelfth day following a missed menstrual period (i.e., about the fortieth day of amenorrhea) giving about a 2 to 6% error when correctly performed, B. M. Hibbard, Brit. Med. J., 1, 593 (1971) and C. A. Horwitz, et al., Obstet. Gynecol., 43, 693 (1974). However, the tests cannot be relied upon prior to that time since they only can detect minimum concentrations of HCG of about 1000–3000 m. i.u./ml of urine. The main reason for not increasing the sensitivity of these test by concentrating urine samples is to avoid false positives resulting from substances which cross react with the HCG-antiserum, B. M. Hobson, J. Reprod. Fertil., 12, 33 (1966).

Recently, more sensitive tests have been developed. These newer tests are based on sensitive but sometimes non-specific radioimmunoassay (RIA) techniques. The nonspecificity of these tests arise from the fact that they also give possitive results with other gonadotropins such as human pituitary luteinizing hormone (LH), i.e., the antisera to HCG may cross react with LH. Using the non-specific RIA techniques, LH–HCG has been shown to rise sharply beginning 10 to 14 days after the mid-cycle LH peak in the first month of pregnancy. For example, see R. B. Jaffe, et al., J. Clin. Endocrinol. Metabol, 19, 1281 (1969); A. F. Parlow, et al., J. Clin. Endocrinol. Metabol., 31, 213 (1970); D. P. Godstein, et al., Fertil., 23, 817 (1972); L. Wide, Lancet, 2, 863 (1969) and D. R. Mishell, Jr., et al., Am. J. Obstet. Gynecol., 117, 631 (1973).

A RIA also has been developed which is specific for the beta subunit of HCG. This latter test has been used to measure serum or plasma HCG by RIA in the presence of circulating LH during the same early period of pregnancy. See, for example, T. S. Kosasa, et al., J. Clin. Endocrinol. Metabol., 36, 622 (1973) and T. S. Kosasa, et al., Obstet. Gynecol., 42, 868 (1973).

Although RIA techniques are sensitive, it will be appreciated that these methods are expensive and complex. They must be performed by highly trained personnel using isotopic material and very sophisticated equipment.

Another test is the radio-receptor assay for HCG recently developed by B. B. Saxena, et al., Science, 184, 793 (1974). Although less time-consuming than the RIA, this test also involves radioactivity, special equipment and an operator with technical skills.

Another group of tests for pregnancy are the biological tests, including the well known "rabbit test". For a review on these and other tests see B. M. Hobson, cited above. It is a well known fact, however, that these biological tests are laborious and time-consuming. Furthermore, they require the maintenance of colonies of animals which are subjected to seasonal variations in sensitivity.

Still other pregnancy tests have been reported. These other tests depend on estimations of serum steroid levels or on the observation of withdrawal bleeding after progestin alone or progestin-estrogen therapy. These tests are considered to be less reliable, and in the case of the latter, unsafe to the subject and conceptus.

In accordance with the need for a simple, sensitive, reliable and safe test for the detection of pregnancy, the present invention provides a method and a device for such a test based on the concept of ultrafiltration of body fluid (e.g., urine, serum or plasma) followed by immunological determination of HCG. Ultrafiltration had been used to concentrate initially high titres of "trophoblastic tumor HCG", in urine. M. L. Taymor, et al., J. Endocrinol., 36, 417 (1966) and S. Lok, Asian J. Med., 9, 319 (1973). Such tumors produce high levels of "trophoblastic HCG", much higher than those encountered in pregnancy. Taymor, et al. concentrated the high "trophoblastic titre HCG" urine in a step directed to the purification of this gonadotropin. Incidentally, these tumors occur only rarely. It should be noted that samples from subjects having trophoblastic tumors will give a positive test in the present invention. Accordingly, in the case where the present method gives a positive test which is later shown to be false in regards to pregnancy, such HCG producing tumors should be suspected.

It is not established whether the chlorionic gonadotropins of pregnancy have carbohydrate and protein structures that are identical to the chorionic gonadotropins secreted by patients with hydatiform male or metastatic carcinoma, R. E. Canfield, et al., Recent progr. Hor. Res, 27, 121 (1971). Several reports have suggested that the urine from patients with chiocarcinoma may contain a gonadotropin that is chemically or immunologically different from the HCG of pregnancy, R. A. Reisfeld and R. Hertz, Biochem. Biophys. Acta, 43, 540 (1960); E. E. Wilde and K. D. Bashawe, Cuba Found. Study Group [Pap,] 22, 46 (1965) and N. Mochizuki, et al., Folia Endocrinol. Jap., 44, 459 (1968).

The present invention provides a convenient method and device for detecting pregnancy, especially in the early stages, the method being reliable and easily performed. Furthermore, the invention provides a method giving a substantial reduction in false negatives and false positives compared to prior art non-radioactive methods.

U.S. Pat. No. 4,033,723 issued July 5, 1977, now U.S. Pat. No. 4,123,224 issued Oct. 31, 1978, of Givner and Schilling, now disclaimed in favor of its continuation, U.S. Ser. No. 808,587 filed June 21, 1977 now U.S. Pat. No. 4,123,224 issued Oct. 31, 1978, herein incorporated by reference, disclose a method and device suitable for the detection of pregnancy, including early pregnancy, based on the ultrafiltration of the biological fluid, selected from the group of urine and serum containing human chlorionic gonadotropin or the β-subunit thereof and detection by immunological means of the concentrate, is provided. The device includes a chamber, opened at the top and closed at the bottom, having the upper portion of at least one wall formed of an ultrafiltration membrane permeable to urine or serum and capable of selective retention of human chorionic gonadotropin, all other walls being formed of a rigid impermeable material, and a layer of absorbent capable of sorbing urine or serum passing through the membrane, the absorbent being contiguous to the outside surface of the membrane and in effective contact with the membrane. The chamber further includes a lower portion, all walls of which are impermeable, for retaining a fixed volume of urine, serum concentrate containing human chorionic gonadotropin, outlet means in the lower portion of the chamber, means for opening the outlet means, and a reagent receptacle connected to the chamber through the outlet means, the reagent receptacle adapted to receive a reagent for the immunological determination of human chorionic gonadotropin or its β-subunit and means for viewing the reaction of the reagent therein with the said urine or serum concentrate containing human chorionic gonadotropin.

A method and device suitable for the detection of human chorionic gonadotropin and pituitary gonadotropins is also described in U.S. Ser. Nos. 786,721 filed Apr. 11, 1977, now U.S. Pat. No. 4,123,509 issued Oct. 31, 1978, and its continuation-in-part U.S. Ser. No. 806,569 filed June 14, 1977, now U.S. Pat. No. 4,123,510 issued Oct. 31, 1978 herein incorporated by reference.

The instant invention comprises carrying out the above described method or treating the above described device such that the concentration by ultrafiltration is conducted in the presence of a particular fraction of polyvinylpyrrolidone.

SUMMARY OF THE INVENTION

According to one aspect of this invention, a simple and sensitive test method for the detection of physiological conditions characterized by the presence of a polypeptide or glycoprotein antigen selected from chorionic gonadotropin, human chorionic gonadotropin, pregnant mare's serum gonadotropin, carcino embryonic antigen, luteinizing hormone, follicle stimulating hormone, human menopausal gonadotropin and thyroid stimulating hormone in the urine or serum of a patient is disclosed. The physiological condition being detected will be associated with the presence of the particular antigen being determined. Illustratively, the method is suitable for the detection of the human chorionic gonadotropin of pregnancy or cancer which is preferably detected in the urine. The method enables detection of the HCG in urine at a concentration as low as 40 m. i.u./ml of urine and is further capable of detecting pregnancy as early as day 26 of a regular 28 day menstrual cycle. Still further, the method enables assessment of pituitary and gonadal function, for instance, ovulation by the detection of LH. The test method includes the steps of:

(a) clarifying a sample of the urine to be tested;
(b) subjecting about 5 to 50 ml of the clarified urine sample to absorbent induced ultrafiltration through an ultrafiltration membrane backed by a layer of absorbent capable of sorbing urine serum passing through the membrane, and said membrane having a molucular weight out-off from about 5,000 to about 200,000 whereby said polypeptide or glycoprotein antigen is retained in the sample;
(c) continuing the ultrafiltration until the retentate sample is one-tenth to one-five hundredth its original volume;
(d) diluting the retentate with sufficient water to provide a retentate sample of about 0.5 ml; and
(e) contacting the retentate sample with the appropriate amount of an immunologic reagent for detecting the presence of said polypeptide or glycoprotein antigen in the retentate sample.

The invention resides in the improvement which comprises contacting said membrane with a dilute solution of polyvinylpyrrolidone prior to or concurrent with ultrafiltration, wherein said polyvinylpyrrolidone has an average molecular weight greater than about 9,000 and less than about 40,000.

In a preferred embodiment the immunologic reagent includes:

(1) Pyruvic aldehyde stabilized erythrocytes sensitized with a polypeptide or glycoprotein antigen selected from chorionic gonadotrophin, human chorionic gonadotropin, pregnant mare's serum gonadotrophin, carcino embryonic antigen, luteinizing hormone, follicle stimulating hormone, human menopausal gonadotrophin and thyroid stimulating hormone, said stabilized erythrocytes being coupled to said antigen with a bifunctional molecule selected from glutaraldehyde, glyoxal, succinialdehyde, hexamethylene diisocyanate, toluene 2,4-diisocyanate, diethyl malonimidate dihydrochloride, dimethyl suberimidate, bis diazotized benzidine, cyanuric chloride, tetrazotized o-anisidine, and 1-ethyl-3-(3-dimethylaminopropyl)carbodiimide; and (2) an antiserum to detect said polypeptide or glycoprotein antigen.

In still another embodiment the immunologic reagent includes a highly purified antiserum to said polypeptide or glycoprotein antigen, or to a subunit, fragment or subfragment thereof which is specific to said polypeptide or glycoprotein antigen. For example, with HCG an antiserum which is specific to be beta subunit thereof could be employed. Further, while the antiserum employed could be secific to the antigen being detected, the antigen may be detected by non-specific but highly purified antiserum which has a known (pre-determined) cross-reactivity to the antigen being detected. Thus, by the method of this invention luteinizing hormone is detected by a luteinizing hormone antiserum or a human chorionic gonadotropin which cross reacts with luteinizing hormone.

DETAILS OF THE INVENTION

The term "molecular cut-off" as used herein refers to the capacity of an ultrafiltration membrane to retain 80 to 100% of those molecules having a molecular weight equal to or greater than the number associated with the term, while allowing those molecules of lesser molecular weight to pass through the membrane.

The term "false positive" as used herein contemplates the occurrence of a positive test result when it can be demonstrated unequivocally by other methods that the test result should be negative.

The term "expected date of menses" as used herein refers to the 28th day after the first day of the last menses.

The term "immunological reagent" means reagents used to perform an agglutination test, or an agglutination inhibition test. In these tests red blood cell or latex particles may be used.

It will be appreciated by those skilled in the immunochemistry art that the immunological determination of the $\beta$-subunit of HCG is possible whether the $\beta$-subunit is separate or incorporated in the HCG molecule. For the purpose of this invention the detection of the $\beta$-subunit in either form is effective.

The first steps of the pregnancy detection method of this invention involves filtering the urine or serum sample, and concentrating the filtered sample by ultrafiltration using a suitable ultrafiltration membrane. In the case of the concentration of urine, a sample preferably from the first morning urination, is used. A number of such ultrafiltration membranes are described by W. F. Blatt in "Methods in Enzymology", Vol., XXII, W. B. Jakoby, Ed., Academic Press, New York and London, 1971; V. E. Pollak, et al., J. Lab. Clin. Med., 71 338 (1968); W. F. Blatt et al., Nature, 216, 511 (1967) and W. F. Blatt, et al., Science, 150, 224 (1965); as well as in U.S. Pat. No. 3,549,016, issued Dec. 22, 1970; and U.S. Pat. No. 3,615,024, issued Oct. 26, 1971.

Examples of suitable ultrafiltration membranes include those of anisotropic, aromatic polymer type, for instance Diaflo PM-10 TM, Diaflo PM-20 TM (Amicon Corp); Diaflo PM-30 TM (Amicon Corp); lopor AP TM and lopar XP TM (Dorr-Oliver, Stamford, Conn.); the anisotropic, cellulosic type, for instance, HFA-100 and HFA-200 (Abcor Inc., Cambridge, Mass.) and PSED (Millipore Corp., Bedford, Mass.); and gel cellophane such as manufactured by du Pont Chemicals, Wilmington, Delaware or Union Carbide, N.Y.C.

Method and apparatus for concentration by ultrafiltration of the aforementioned sample are described in the above references pertaining to ultrafiltration membranes. Particularly useful designs for ultrafiltration concentrators are described also by E. M. Zipilivan, et al., in U.S. Pat. No. 3,817,379, issued June 18, 1974. This reference is herein incorporated in its entirety by reference.

Thereafter, the present method involves the detection of HCG in the concentrated sample. Preferred test methods for determining the presence of HCG in the concentrated urine or serum sample are the tests using immunological reagents.

The agglutination tests, for example, see H. Fink and A. Frie, Obstet. Gynecol, 28, 660 (1966), are based on the direct reaction between HCG and a HCG-antibody.

The agglutination inhibition tests are based on an inhibition of a reaction between HCG-antiserum and HCG on a carrier, for instance, red blood cells or latex particles. When the latter test involves red blood cells it is known as the haemagglutination inhibition test and when the latter test involves latex particles it is known as the latex agglutination inhibition test. For example, see L. Wide and C. A. Gemzell, Acta Endocrinol, 35, 261 (1960); B. M. Hobson, J. Reprod. Fert., 12, 33 (1966) and references cited herein; B. M. Hibbard, Brit. Med. J., 1, 593 (1971); U.S. Pat. No. 3,548,051, issued Dec. 15, 1970; U.S. Pat. No. 3,551,555 issued Dec. 29, 1970; and U.S. Pat. No. 3,666,421, issued May 30, 1972.

The HCG-antibody, required for the above tests, is known. The preparation of the antibody have been described several times, for example, see Wide and Gemzell, cited above, and A. R. Midgley, et al., Proc. Soc. Exp. Biol. Med., 108, 85 (1961). If desired HCG also can be detected by using a specific antiserum to the $\beta$-subunit of HCG, see J. Vaitukaitis, et al., J. Clin. Endocrinol., 33, 988 (1971) and Amer. J. Obstet. Gynecol., 113, 751 (1972). When the specific antiserum to the $\beta$-subunit of HCG is used, it will of course detect the presence of the $\beta$-subunit itself as well as intact HCG. (It is well known that the $\beta$-subunit of HCG readily dissociates from HCG.)

Test kits suitable for the detection of HCG in urine and serum samples according to the method of this invention are available commercially; for example, the haemagglutination inhibition test kits, for instance, Pregnosticon All-in TM (Organon, Holland and U.S.A.) and UCG TM (Wampole Laboratories, Stamford, Conn.); latex agglutination inhibition test kits, for instance, Planotest TM, Pregnosticon Dri-Dot TM (Organon, Holland and U.S.A.), Gravindex TM (Ortho, Raritan, N.J., U.S.A.) and Prepurex TM or Prepurin TM (Burroughs Wellcome, U.S.A. and United Kingdom); and the direct agglutination test, for instance, DAP Test (Denver Biologicals Co. U.S.A.) and Gonavislide (Molter Gmbh., West Germany).

Other immunological reagents useful in the present invention are those described in U.S. application Ser. No. 806,562 now U.S. Pat. No. 4,123,343 issued Oct. 31, 1978, and U.S. application Ser. No. 806,563, both filed June 14, 1977 herein incorporated by reference. These reagents are characterized by (1) pyruvic aldehyde stabilized erythrocytes sensitized with a polypeptide or glycoprotein antigen selected from chorionic gonadotrophin, human chorionic gonadotrophin, pregnant mare's serum gonadotrophin, carcino embryonic antigen, luteinizing hormone, follicle stimulating hormone, human menopausal gonadotrophin and thyroid stimulating hormone, said stabilized erythrocytes being coupled to said antigen with a bifunctional molecule selected from glutaraldehyde, glyoxal, succinialdehyde, hexamethylene diisocyanate, toluene 2,4-diisocyanate, diethyl malonimidate dihydrochloride, dimethyl suberimidate, bis diazotized benzidine, cyanuric chloride, tetrazotized o-anisidine, and 1-ethyl-3-(3-dimethylaminopropyl)carbodiimide; and (2) a highly purified antiserum to human chorionic gonadotrophin or the beta subunit thereof.

In a preferred embodiment said bifunctional molecule is selected from glutaraldehyde and hexamethylene diisocyanate.

These reagents are advantageously utilized in the form of lyophylized pellets or cakes, preferably pellets.

Polyvinylpyrrolidone (PVP) is a well known commercial product produced commercially as a series of products having mean molecular weights ranging from about 10,000 to 700,000. Prepared by Reppe's process: 1,4-butanediol obtained in the Reppe butadiene synthesis is dehydrogenated over copper at 200° forming γ-butyrolacetone; reaction with ammonia yields pyrrolidone. Subsequent treatment with acetylene gives the vinyl pyrrolidone monomer. Polymerization is carried out by heating in the presence of $H_2O_2$ and $NH_3$. DeBell et al., German Plastics Practice (Springfield, 1946); Hecht, Weese, Munch. Med. Wochenschr. 1943, 11; Weese, Naturforschung & Mediazin 62, 224 (Wiesbaden, 1948), and the corresp vol. of FIAT Review of German Science. Monographs: General Aniline and Film Corp., PVP (New York, 1951); W. Reppe, Polyvinylpyrrolidon (Monographie zu "Angewandte Chemie" no. 66, Weinheim/Bergstr., 1954). Generally available commercial grades have average molecular weights in the range of 10,000 to 360,000, for example, General Aniline and Film Corporation (GAF) markets at least four viscosity grades available as K-15, K-30, K-60, and K-90 which have average molecular weights of about 10,000, 40,000, 160,000 and 360,000, respectively.

K-values are derived from viscosity measurements and calculated according to Kikentscher's formula (Kline, G. M. Modern Plastics 137 No. 1945):

$$\frac{\log \eta rel}{c} = \frac{75K_o^2 + K_o}{1 + 1.5K_o c}$$
$$K = 1000K_o$$

where
  c=concentration in g/100 ml solution
  ηrel=viscosity of solution compared with solvent
The molecular weight of PVP samples has been determined by osmometry, in the ultracentrifuge, by light-scattering measurements, thermodiffusion methods, sedimentation constants, turbidity tritrations, and viscosity techniques.

The particular fraction of PVP useful in the present invention is that fraction having an average molecular weight greater than about 9,000 and less than about 40,000, preferably an average molecular weight from about 28,000 to about 35,000, particularly useful is viscosity grade K/26-28 marketed by GAF having an average molecular weight of about 33,000. The manufacture of this viscosity grade is disclosed in U.S. Pat. Nos. 2,265,450 and 2,335,454 herein incorporated by reference. A similar commercial product is available from BASF-Wyandotte.

More specifically, in practising the method of this invention for detecting HCG, a sample of female urine or serum, the urine preferably being clarified by filtration through a suitable filter paper or by centrifugation, is concentrated 10 to 500 times, preferably 10 to 50 times by placing the sample in contact with an ultrafiltration membrane having a molecular weight cut-off ranging from about 10,000 to about 50,000, preferably about 15,000 to 35,000. In other words, a lower limit of 10,000 or preferably 15,000 and an upper limit of 50,000, preferably an upper limit of 35,000, have been found useful. The sample is filtered through the membrane until the unfiltered portion of the sample (retentate) has reached the desired degree of concentration. The concentration step is carried out usually at temperatures ranging from about 0° to 40° C., preferably 4° to 25° C. and usally takes half an hour to two hours. The filtrate is discarded and the retentate is subjected to an immunological test for HCG. For convenience in performing immunological test, the retentate is diluted with sufficient water to provide a retentate sample of about 0.5 ml if the retentate is less than this volume.

In practicing the method of this invention for detecting said polypeptide or glycoprotein antigens, other than HCG, the molecular weight cut-off of the ultrafiltration membrane employed to concentrate the sample will range from about 5,000 to about 50,000, preferably from about 10,000 to about 35,000. For carcino embryonic antigen which has a molecular weight of about 200,000, the upper limit of the membrane molecular weight cut-off can be up to about 200,000. It will be appreciated by one skilled in the art that the choice of a membrane having a particular molecular weight cut-off will further depend on the molecular weight of the antigen to be detected, the specificity of the immunologic reagents employed, and the presence of interfering substances in the sample.

The aqueous solution of the concentrated urine or serum is mixed in an ampoule-tube or on a slide with the regularly recommended amount of immunological reagent.

In the case of the tube test, after allowing the mixture to stand for about one to two hours, a positive reaction is indicated by a specific sedimentation pattern in the form of a clearly defined ring at the bottom of the tube if it is round bottomed or in the form of a dot if it has a conical-shaped bottom; a negative reaction is indicated by a diffuse yellow-brown sediment.

Alternatively, latex agglutination inhibition or direct agglutination tests, with their characteristic visual endpoints, see above, are used for the detection of HCG in the aqueous solution of concentrated urine.

In the practice of this invention, it has been found advantageous to subject the inner surface of the concentrator, i.e., the chamber containing the ultrafiltration membrane, to a prewash with a 0.5 to 4% preferably 1.0 to 2.0% aqueous solution of polyvinylpyrrolidone (PVP) to contact the inner surfaces of the concentrator prior to placing the sample of urine in the cocentrator. This modification significantly improves the sensitivity of the present method by preventing adsorption losses of HCG on the surface of the device (thereby reducing the number of false negatives) and improves the replication of the test. The latter aspect is of paramount importance when only single tests are performed.

For example, units equivalent to the Minicon B-15 were pre-rinsed with a 1% weight by volume PVP solution of each of viscosity grades K-15, K-26-28, K-30 and K-60. The units were then employed in the procedure outlined above using HCG spiked urine from a cycling female. With K-15 pre-washed units, the recoveries of HCG in the retentate were inadequate and the results marginal. With K-60 pre-washed units, results were not acceptable. With K-30 pre-washed units, the ring is not sharply defined and results were unsatisfactory. With the K/26-28 pre-washed units, the recoveries of HCG were high, retentate volume was maintained over an extended period of time, and the results were excellent in terms of a clearly defined ring at the bottom of the tube.

Furthermore, it has been found that the same advantageous results are obtained if the 0.5-4.0% weight by volume PVP solution is used to wash the aforementioned filter paper used to filter the urine or serum sample of if PVP is added directly to the initially collected urine sample to give a concentration ranging from 0.01 to 2.0%, preferably 0.1 to 1.0% PVP in the urine.

Although it may appear obvious to concentrate a dilute solution of HCG so that the concentration of HCG falls within the sensitivity range of a given test, it is in direct contradiction to the cumulative experience with immunological tests for the determination of HCG in body fluids. In the first place it will be appreciated that concentration of such body fluids as urine and serum likewise concentrates those substances which interfere with the immunological test. Secondarily, there is good authority that concentration of body fluids such as urine increases the occurrence of false positives; see, for example, L. Wide, Acta Endocrinol., Suppl, 70 (1962) p. 95 and 100, and M. Hobson, cited above, p. 43.

More explicitly, Wide recommends strongly that immunological tests be adjusted so that a positive test be obtained only when the cocentration of HCG in urine is 1000 or more m.I.U./ml. Otherwise, the levels of LH or human menopausal gonadotropin, occurring in some samples, may interfere with the specificity of the HCG assay leading to false positives.

One attempt to overcome the situation is described by R. T. Fisk in U.S. Pat. No. 3,171,783, issued Mar. 2, 1965. According to the method of the Fisk Patent, which is much more complicated than the ultrafiltration method of the present invention, HCG in the urine is concentrated by absorption on Kaolin. However, after adsorption of the HCG according to this procedure at least three more steps must be carried out before proceeding with an immunological test for HCG. A similar elaborate technique based also on absorption of kaolin was described earlier by E. H. Hon and J. McL. Morris, Yale J. Biol. Med., 27, 178 (1954). Further evidence for the complexity of these two methods are that they have never been used widely by practitioners, see Hobson, cited above, and Hibbard, cited above. Furthermore, these latter methods and another related method of the prior art, B. M. Hobson and L. Wide, Acta Endocrinol., 46, 632 (1964), result in about a 50% loss of activity of the gonadotropin with a consequential loss of sensitivity; also the chance of obtaining false negatives and false positives (e.g. urine samples from premenopausal, menopausal or post-menopausal women) is increased.

A device useful in the method of the present invention is shown in several embodiments in FIGS. 1-14 of the accompanying drawings wherein:

The device of this present invention is shown in several embodiments in FIGS. 1-14 of the accompanying drawings wherein:

FIG. 1 represents a perspective view of the inner and outer components of one embodiment of the device in separated spaced relationship prior to insertion of the former into the latter;

FIG. 2 represents a vertical cross-sectional view of the inner and outer components of FIG. 1 in fixed operational relationship prior to urine concentration;

FIG. 3 represents a vertical cross-sectional view of the inner and outer components of FIG. 1 in operational relationship subsequent to urine concentration with the inner component partially withdrawn;

FIG. 4 represents a horizontal cross-sectional view along line 4—4 of FIG. 2;

FIG. 5 represents an enlarged partial section of FIG. 2 additionally showing the urine concentrate;

FIG. 6 represents a vertical cross-sectional view similar to FIG. 2 of another embodiment of the device of this invention for use with a pre-selected urine volume;

FIG. 6A heads up a sheet of the accompanying drawings;

FIG. 7 represents a vertical cross-sectional view of an embodiment similar to that shown in FIG. 6 but including a separable reagent chamber; FIG. 7 is found on the sheet of accompanying drawings beginning with FIG. 5;

FIG. 9 represents a cross-sectional view of the separated reagent chamber of FIG. 7 mounted for analysis; FIG. 9 is found on the sheet of accompanying drawings beginning with FIG. 5;

FIG. 10 represents a vertical cross-sectional view of a further embodiment of the device of this invention;

FIG. 11 represents a horizontal cross-sectional view taken along line 11—11 of FIG. 10;

FIG. 12 represents a perspective view of the membrane, including the impermeable lower section thereof, of the embodiment of FIG. 10;

Figure 6A:
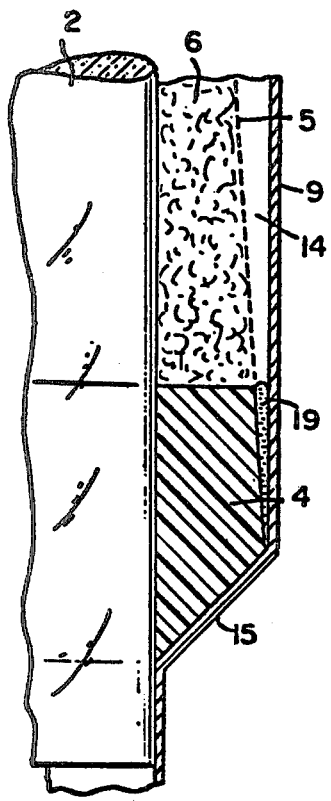
FIG. 6A represents an enlarged partial section of FIG. 6 similar to FIG. 5.

In one exemplified embodiment of the method of this invention, concentration of a urine sample is effected by the use of a Minicon-B-15 TM ultrafiltration concentrator supplied by Amicon Corporation, Lexington, Massachusetts, U.S.A. According to the manufacturer the Minicon-B-15 concentrator is based on the principle of backing an anisotropic Diaflo TM ultrafiltration membrane having a molecular cut-off of 15,000, with absorbent pads. In another run, the Minicon-PM-30 TM, made by the same manufacturer was used; this concentrator is made on the same principle as the Minicon-B-15 TM and has a molecular cut-off of 30,000. Concentrators of this particular design are described in U.S. Pat. No. 3,817,379, cited above.

With reference to the present embodiment, a five ml. sample of first voided morning urine, filtered through Whatman #1 filter paper, was concentrated by placing the sample in a well of the Minicon-B-15 TM concentrator. During the concentration step the concentrator was allowed to stand in an ambient temperature, room temperature or about 4° C. After a period of about two hours the sample had concentrated to about 0.1 ml. The concentrated urine (retentate) was removed from the concentrator and diluted back to a volume of 0.5 ml with distilled water to give the aqueous solution of the concentrated urine. Removal of the retentate was done by using a fine Pasteur pipette. Thereafter, the aqueous solution of concentrated urine was tested for the presence of HCG by a test for determining HCG in urine.

Turning now to FIG. 1, inner component 1 is comprised of rod 2, spaced apart collars 3 and 4 connected by ultrafiltration membrane 5 surrounding absorbent 6. Rod 2 is equipped with handle 7 for ease of insertion and withdrawal and an end portion projecting beyond collar 4 to act as a plug. Collar 3 and 4 surround rod 2, collar 4 being fluid impermeably sealed to rod 2 and collar 3 being so fitted as to allow for escape of air from absorbent 6.

Outer component 8 is comprised of inner and outer walls 9 and 10, respectively, joined by member 11 to provide a funnel shaped top opening 12. Inner and outer walls 9 and 10 enclosed absorbent 13.

Referring to FIG. 2, outer component 8 is adapted to receive inner component 1 to provide annular space 14 and is adpated in its lower portion by wall 15 to receive collar 4 and the lower end portion of rod 2 in fluid impermeable sealed relationship. Outer component 8 includes integrally therewith an appeding reagent receptacle 17 containing reagent 17a. Also inner wall 9 of outer component 8 has an opening 18 through wall 9 leading to absorbent 13.

In utilizing the embodiments of the invention shown in FIGS. 1 through 5 to test for pregnancy, a urine sample of a woman is filtered, for example, through Whatman No. 1 filter paper or centrifuged, for example, at 3000 rpm for 5 minutes, and poured into funnel shaped top opening 12 of the unit as shown in FIG. 2. The urine flows down and fills annular space 14 and any excess over, for example, 5 ml, flows through opening 18 and is absorbed by absorbent 13. The ultrafiltration membrane 5 is selected to provide a molecular weight cut-off of about 10,000 to 50,000, preferably 15,000 to 35,000, so as not to permit passage of human chorionic gonadotropin. Such membranes are described above.

A portion of the urine in annular space 14 passes through ultrafiltration membrane 5 and is absorbed by absorbent 6, the displaced air escaping unwardly past collar 3. When the level of concentrate in annular space 14 reaches the upper surface of collar 4, i.e. impermeable dead stop zone, after about two hours, no further concentration can take place as shown at 19 in FIG. 5 and the concentrate comprises a predetermined amount, for example 0.5 ml. Inner component 1 is lifted from outer component 8 permitting passage of the concentrate around the end portion of rod 2 projecting beyond collar 4 (i.e., the plug portion of rod 2) and into receptacle 17.

Positioned in receptacle 17 is reagent 17a which is a lyophilized mixture of HCG or β-HCG antiserum, erythrocytes, buffer, preservative and excipients.

Figure 6B:
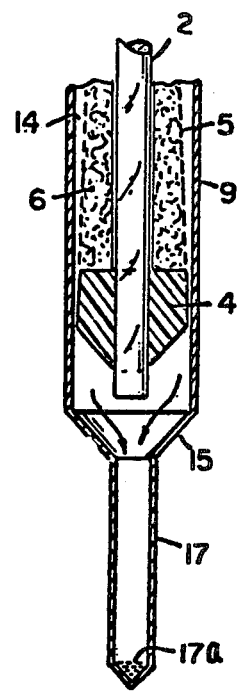
FIG. 6B represents a partial vertical cross-sectional view similar to FIG. 3 of the embodiment of FIG. 6.
Figure 6C:
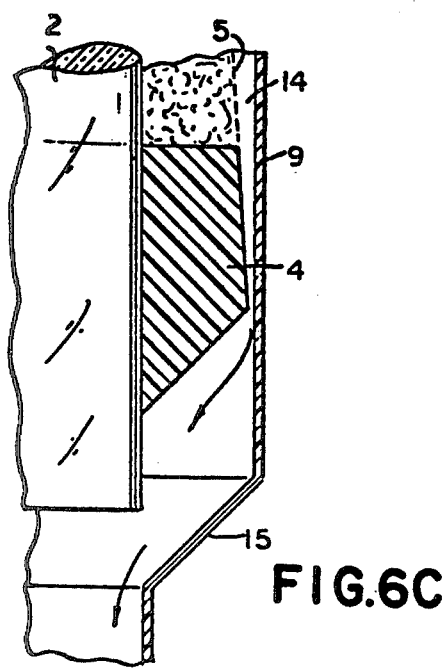
FIG. 6C represents an enlarged partial section of FIG. 6B.
Figure 8:
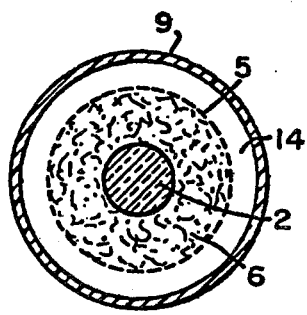
FIG. 8 is a horizontal cross-sectional view taken along line 8—8 of FIG. 6.

After one to two hours (tube test), a reading is made and if the woman is pregnant, a specific sedimentation pattern in the form a clearly defined ring or dot appears depending on the shape of the bottom of the receptacle 17, i.e., round-bottom or wedged shape. If no ring or dot appears, the female is not pregnant. For reading the test results, the rod 2 can be made of glass or a clear plastic material such that the ring or dot can be viewed by the operator by sighting down the rod. In this circumstance, the lower portion of chamber 17 is made of a translucent material. A mirror 20 disposed under chamber 17 as shown in FIG. 6 simplifies reading the test results.

FIGS. 6, 6A, 6B, 6C and 8 show an alternative embodiment wherein the device is not equipped for overflow and requires premeasurement of the urine sample. Thus inner component 1 is the same and the outer component does not include outer wall 10 and absorbent 13.

Figure 7A:
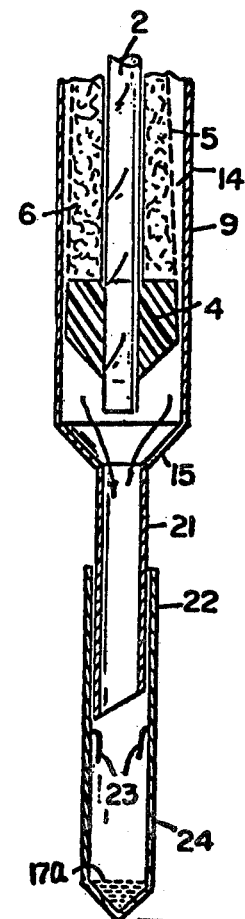
FIG. 7A represents a vertical cross-sectional view of the embodiment of FIG. 7 with the inner component partially withdrawn.

FIGS. 7, 7A and 9 show an alternative embodiment wherein component 1 is the same and the outer component is constructed in two pieces. Thus in FIG. 7, the outer component is comprised of wall 9, lower portion wall 15 and spout 21. Below and slideably surrounding spout 21 is receptacle 22 having closure membrane 23 defining a closed section 24 containing reagent 17a.

In FIG. 7A, membrane 23 is shown ruptured after further insertion into receptacle 22 of spout 21, and inner component 1 in partially withdrawn or raised position.

FIG. 9 shows the receptacle 22 separated from spout 21 of FIG. 7 mounted on support rack 25 also containing mirror 20.

In the embodiment of FIGS. 10 and 11 the chamber 26 is in the form of a right square prism and is defined by impermeable walls 27, 28, 29 and 30 and within chamber 26 is positioned pyramidally shaped, utrafiltration membrane 31, surrounded on its outside periphery by absorbent 32. Within the space 32a defined by pyramidally shaped membrane 31 (including the fluid impermeable pyramidally shaped lower section 32b, i.e. the impermeable "dead stop zone") is positioned ampoule 33 containing reagent 34 maintained under vacuum. In the lower section 32b is a depression 35 adapted to receive snugly the stem 36 of ampoule 33. In this embodiment the stem 36 is prestressed at the point 32c which corresponds to the bottom of impermeable lower section 32b.

The pyramidally shaped form of member 31 including its lower section 32b for the embodiment of FIGS. 10 and 11 is shown in FIG. 12.

In operation of the embodiment of FIG. 10, urine is introduced into space 32a surrounding ampoule 33 and is concentrated to a retentate. The ampoule 33, fitted snugly in depression 35, is then broken at the prestressed point. The retentate is necessarily drawn into previously evacuated ampoule 33 and contacts reagent 34; the ampoule 33 is inverted, contents mixed thoroughly, and then placed in a rack to be viewed.

Figure 13:
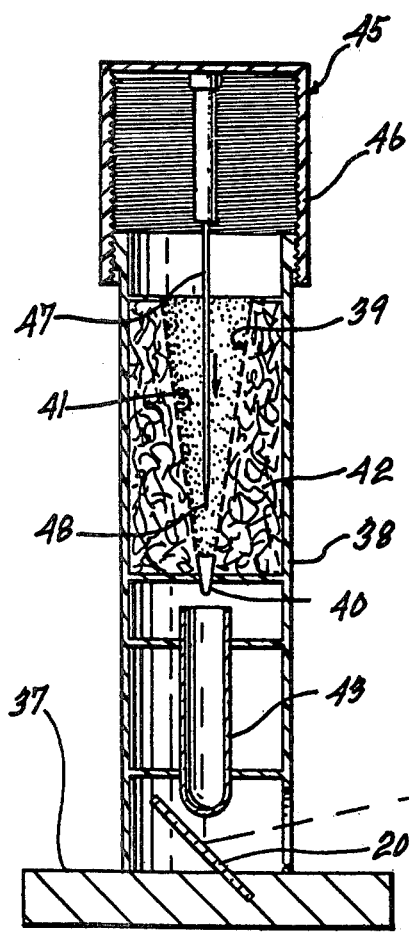
FIG. 13 represents a vertical cross-sectional view of still a further embodiment of the device of this invention.

In still another embodiment of the device of this invention, reference is made to FIG. 13. In FIG. 13, a base 37 is shown supporting outer wall 38. Outer wall 38 supports a cone shaped member 39, the lower portion 40 of said member 39 is formed of a fluid impermeable material and the upper portion 41 of said member 39 is formed of an ultrafiltration membrane. Positioned adjacent to membrane 41 is absorbent 42 in effective contact with the outside surface of the membrane 41. Disposed beneath the impermeable portion 40 of cone shaped member 39 is reagent receptacle 43 and disposed beneath receptacle chamber 43 is mirror 20. The portion of outer wall 38 surrounding the receptacle and the receptacle itself are made of a material transparent to light. Positioned above outer wall 38 is cap 45 having depending therefrom circumferential wall 46 and plunger 47 with a pointed tip 48.

In operation, urine is measured into cap 45, the urine is poured into cone shaped member 39, the fluid passes through upper portion 41 and into absorbent 42 and the retentate is collected within impermeable lower portion 40. When the retentate has collected, cap 45 is formed down, as by being threadedly engaged, such that the point 48 of plunger 47 ruptures impermeable wall 40 of member 39. When the plunger 47 is withdrawn, the retentate flows through the rupture and into reagent receptacle 43. The reaction can be read by removing the reagent receptacle or by means of a mirror 20 placed beneath reagent receptacle 43.

Figure 14:
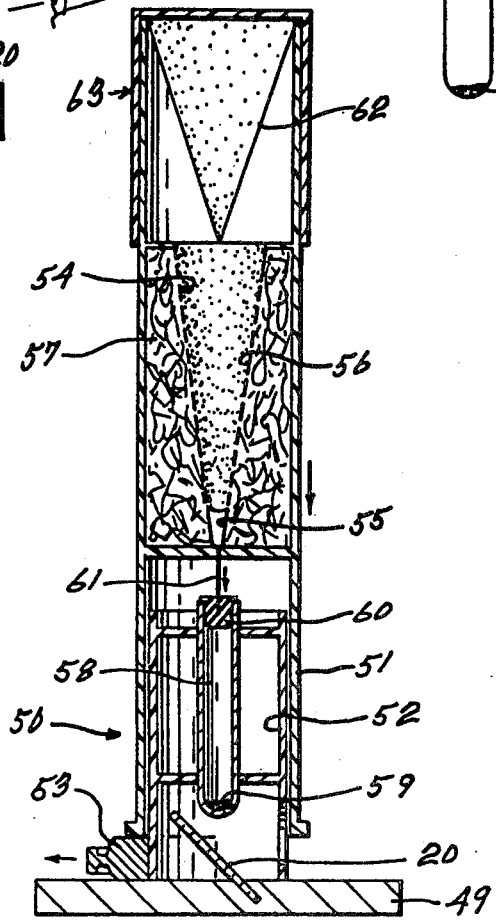
FIG. 14 represents a vertical cross-sectional view of still another embodiment of the device of this invention.

Still another embodiment is illustrated by FIG. 14. This embodiment comprises a base 49 supporting telescopic member 50. Telescopic member 50 consists of a outer wall member 51 and an inner wall member 52; the latter being slideably received in the former. Removable abutment member 53 is placed between the outer wall member 51 and the base 49 to position the outer and inner wall members 51 and 52 with respect to each other. Outer wall member 51 supports pyramidally shaped member 54; the lower portion 55 of said member 54 being in the form of a fluid impermeable material and the upper portion 56 of said member 54 being an ultrafiltration membrane. Positioned adjacent to member 54 is absorbent 57 in effective contact with the outer surface of the upper portion of membrane 56. Disposed below impermeable portion 55 and supported by brackets positioned on the lower wall member 52 is reagent receptacle 58 containing the reagent 59 maintained under vacuum by rubber seal 60. A hollow tube 61 depends from the bottom of the lower impermeable portion 55 and said tube is in fluid-flow communication with said lower portion 55, seal 60 sealing the bottom of the tube 61. Positioned over the upper portion 54 and supported by outer wall member 51 is filtered 62. The device of this embodiment is provided further with removable dust cap 63, and mirror 20 disposed below the reagent receptacle 58.

In operation, a predetermined quantity of urine is filtered through the filter 62 and is collected in pyramidally shaped member 54. Sorbable fluid passes through the upper portion 56 into absorbent 57 and the retentate collects in fluid impermeable lower portion 55. When the retentate has collected, abutment member 53 is removed and upper wall is pushed down toward base 49 so that the lower tip of the hollow rod 61 ruptures the seal 60 and the retentate flows by vacuum assistance into the reagent receptacle 58. The device is separated by withdrawing outer wall member 51 up and away from the inner wall member 52 leaving a lower portion of the device comprising base 49, inner wall member 52, mirror 20 and reagent receptacle 58. After the reaction between the retentate and reagent has occurred, the results of the reaction are read by means of mirror 20 positioned below the receptacle 58.

Figure 15:
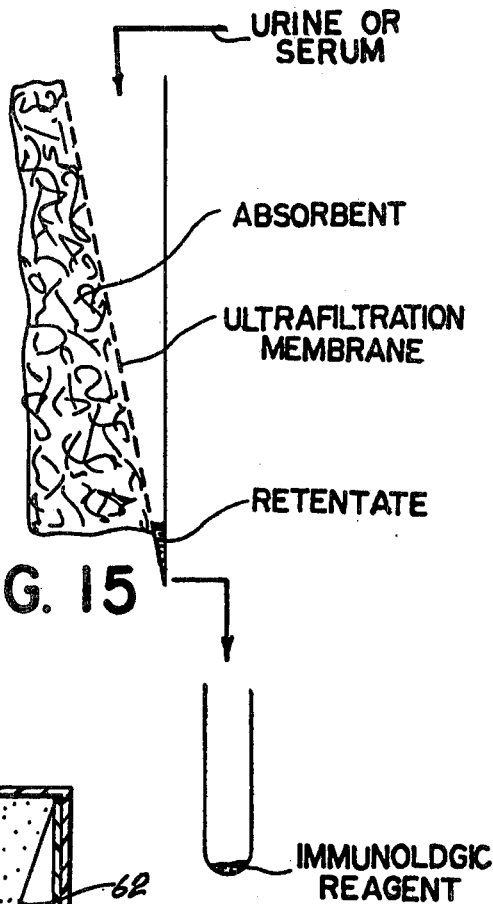
FIG. 15 is a schematic representation of the invention.

FIG. 15 represents schematically the steps of concentrating gonadotropin-containing urine or serum with the ultrafiltration membrane, said membrane being in effective contact with an absorbent capable of sorbing biological fluid to obtain a retentate, and reacting the retentate with a reagent capable of detecting the presence of the gonadotropin.

With reference to the materials useful for the manufacture of the device of this invention a description of the ultrafiltration membrane and the absorbent is found in the above noted references on ultrafiltration membranes, for example, see U.S. Pat. No. 3,817,379, noted above.

Regarding the portions of the apparatus other than the ultrafiltration membrane, the apparatus may be made from any suitable impermeable material which can be molded easily into the desired shape. Glass or plastic can be used. A thermoplastic material or catalytically cured plastic for instance, polyethylene, polypropylene or polystyrene, is most economical and adequate for this purpose.

The success of the method of this invention, its capability of detecting very minute quantities of HCG with very high degrees of sensitivity, accuracy and reproducibility, the significant reduction of false negatives, and the reduction of false positives are predicated upon the selection of a suitable ultrafiltration membrane. The membrane allows the passage of inert materials and of substances interfering with the subsequent immunological test into the filtrate, while retaining the HCG present in the sample of body fluid. In this manner I have succeeded in establishing the presence of pregnancy as early as the 26th day of a regular 28-day menstrual cycle without having to resort to RIA or the radioreceptor method. In some cases this means that pregnancy is being detected as early as 12 days after conception whereas most pregnancy tests available today do not detect pregnancy until about 24 to 26 days after conception.

An alternative embodiment of the present invention is the employment of the above method for the assessment of pituitary and gonadal function, for instance, ovulation, by using antibodies that react with LH.

Still other alternative embodiments include the employment of the method for determining estrogen deficiency states in humans using antibodies to the human gonadotropins, follicle-stimulating hormone (FSH), luteinizing hormone (LH) and human menopausal gonadotropin (HMG).

Thus, by the method of this invention FSH or HMG can be detected in urine at a concentration as low as about 15 m. i.u./ml of urine and LH may be detected at a concentration as low as about 25 m. i.u./ml of urine.

Appropriate antibodies, i.e., anti-LH, N. R. Moudgal and H. G. Madwa Raj, Pituitary Gonadotrophins in "Methods of Hormone Radioimmunoassay", B. M. Jaffe and H. R. Behrman, Ed., Academic Press, New York, 1974, page 75; anti-FSH, A.H.W.M. Schuurs and C. J. Van Wijngaarden, J. Clin, Endocrinol. Metabol., 40, 619 (1975); and anti-HMG, B. Lunenfeld, et al., J. Clin. Endocrinol. Metabol., 21, 478 (1961), and antigens (LH, FSH or HMG) would replace HCG antibody and antigen as elements for these alternative embodiments.

What is claimed:

1. In a diagnostic test method suitable for the detection of physiological conditions characterized by the presence of a polypeptide or glycoprotein antigen selected from chorionic gonadotropin, human chorionic gonadotropin, pregnant mare's serum gonadotropin, carcino embryonic antigen, luteinizing hormone, follicle stimulating hormone, human menopausal gonadotropin and thyroid stimulating hormone in urine including:

(a) clarifying a sample of the urine to be tested;
(b) subjecting about 5 to 50 ml of the clarified urine sample to absorbent induced ultrafiltration through an ultrafiltration membrane backed by a layer of absorbent capable of sorbing urine serum passing through the membrane, and said membrane having a molecular weight with cut-off from about 5,000 to about 200,000, whereby said polypeptide or glycoprotein antigen is retained in the sample;
(c) continuing the ultrafiltration until the retentate sample is one-tenth to one-five hundredth its original volume;
(d) diluting the retentate with sufficient water to provide a retentate sample of about 0.5 ml; and
(e) contacting the retentate sample with the appropriate amount of an immunologic reagent for detecting the presence of said polypeptide or glycoprotein antigen in the retentate sample, with the proviso that when said antigen is human chorionic gonadotropin, then the immunologic reagent comprises other than pyruvic aldehyde stabilized erythrocytes sensitized to human chorionic gonadotropin with a bifunctional molecule;

the improvement which comprises contacting said membrane with a dilute solution of polyvinylpyrrolidone prior to or concurrent with ultrafiltration, wherein said polyvinylpyrrolidone has an average molecular weight greater than about 9,000 and less than about 40,000.

2. In a diagnostic test method suitable for the detection of physiological conditions characterized by the presence of a polypeptide or glycoprotein antigen selected from chorionic gonadotropin, human chorionic gonadotropin, pregnant mare's serum gonadotropin, carcino embryonic antigen, luteinizing hormone, follicle stimulating hormone, human menopausal gonadotropin and thyroid stimulating hormone in urine including:

(a) clarifying a sample of the urine to be tested;
(b) subjecting about 5 to 50 ml of the clarified urine sample to absorbent induced ultrafiltration through an ultrafiltration membrane backed by a layer of absorbent capable or sorbing urine passing through the membrane, and said membrane having a molecular weight cut-off from about 5,000 to about 50,000, whereby said polypeptide or glycoprotein antigen is retained in the sample;
(c) continuing the ultrafiltration until the retentate sample is one-tenth to one-five hundredth its original volume
(d) diluting the retentate with sufficient water to provide a retentate sample of about 0.5 ml; and
(e) contacting the retentate sample with the appropriate amount of an immunologic reagent for detecting the presence of said polypeptide or glycoprotein antigen in the retentate sample, with the proviso that when said antigen is human chorionic gonadotropin, then the immunologic reagent comprises other than pyruvic aldehyde stabilized erythrocytes sensitized to human chorionic gonadotropin with a bifunctional molecule;

the improvement which comprises pre-washing said membrane with about 0.5% to about 4.0% solution of polyvinylpyrrolidone prior to ultrafiltration, wherein said polyvinylpyrrolidone has an average molecular weight greater than about 9,000 and less than about 40,000.

3. In a diagnostic test method suitable for the detection of physiological conditions characterized by the presence of a polypeptide or glycoprotein antigen selected from chorionic gonadotropin, human chorionic gonadotropin, pregnant mare's serum gonadotropin, carcino embryonic antigen, luteinizing hormone, follicle stimulating hormone, human menopausal gonadotropin and thyroid stimulating hormone in urine including:

(a) clarifying a sample of the urine to be tested through a filter;
(b) subjecting about 5 to 50 ml of the clarified urine sample to absorbent induced ultrafiltration through an ultrafiltration membrane backed by a layer of absorbent capable of sorbing urine serum passing through the membrane, and said membrane having a molecular weight cut-off from about 5,000 to about 50,000, whereby said polypeptide or glycoprotein antigen is retained the sample;
(c) continuing the ultrafiltration until the retentate sample is one-tenth to one-five hundredth its original volume;
(d) diluting the retentate with sufficient water to provide a retentate sample of about 0.5 ml; and
(e) contacting the retentate sample with the appropriate amount of an immunologic reagent for detecting the presence of said polypeptide or glycoprotein antigen in the retentate sample, with the proviso that when said antigen is human chorionic gonadotropin, then the immunologic reagent comprises other than pyruvic aldehyde stabilized erythrocytes sensitized to human chorionic gonadotropin with a bifunctional molecule;

the improvement which comprises pretreating said filter with about a 0.5% to about 4.0% solution of polyvinylpyrrolidone prior to ultrafiltration, wherein said polyvinylpyrrolidone has an average molecular weight greater than about 9,000 and less than about 40,000.

4. In a diagnostic test method suitable for the detection of physiological conditions characterized by the presence of a polypeptide or glycoprotein antigen selected from chorionic gonadotropin, human chorionic gonadotropin, pregnant mare's serum gonadotropin, carcino embryonic antigen, luteinizing hormone, follicle stimulating hormone, human menopausal gonadotropin and thyriod stimulating hormone in urine including:

(a) clarifying a sample of the urine to be tested through a filter;
(b) subjecting about 5 to 50 ml of the clarified urine sample to absorbent induced ultrafiltration through an ultrafiltration membrane backed by a layer of absorbent capable of sorbing urine serum passing through the membrane and said membrane having a molecular weight cut-off from about 5,000 to about 50,000, whereby said polypeptide or glycoprotein antigen is retained in the sample;
(c) continuing the ultrafiltration until the retentate sample is one-tength to one-five hundredth is original volume;
(d) diluting the retentate with sufficient water to provide a retenate sample of about 0.5 ml; and
(e) contacting the retentate sample with the appropriate amount of an immunologic reagent for detecting the presence of said polypeptide or glycoprotein antigen in the retentate sample, with the proviso that when said antigen is human chorionic gonadotropin, then the immunologic reagent comprises other than pyruvic aldehyde stabilized erythrocytes sensitized to human chorionic gonadotropin with a bifunctional molecule;

the improvement which comprises contacting said urine sample before of after clarification with a sufficient amount of polyvinylpyrrolidone to give a concentration of the polyvinylpyrrolidone in the urine of from about 0.01% to about 2.0%, wherein said polyvinylpyrrolidone has an average molecular weight greater than about 9,000 and less than about 40,000.

5. The method of claim 1, 2 or 3 suitable for the detection of human chorionic gonadotropin of pregnancy or cancer in urine at a concentration as low as about 40 m.I.U./ml of urine and capable of detecting pregnancy as early as day 26 of a regular 28 day menstrual cycle wherein said membrane has a molecular weight cut-off from about 15,000 to about 35,000; the average molecular weight of said polyvinylpyrrolidone is from about 28,000 to about 35,000; and the concentration of the dilute solution of polyvinylpyrrolidone is from about 0.5% to about 4.0%, weight by volume.

6. The method of claim 1, 2 or 3 for the detection of human chorionic gonadotropin wherein said membrane has a molecular weight cut-off from about 15,000 to about 35,000; the average molecular weight of said polyvinylpyrrolidone is from about 28,000 to about 35,000 and the concentration of the dilute solution of polyvinylpyrrolidone is from about 1.0% to about 2.0%, weight by volume.

7. The method of claim 1, 2 or 3 suitable for the detection of human chorionic gonadotropin of pregnancy or cancer in urine at a concentration as low as about 40 m.I.U/ml of urine and capable of detecting pregnancy as early as day 26 of a regular 28 day menstrual cycle wherein said membrane has a molecular weight cut-off from about 15,000 to about 35,000; the average molecular weight of said polyvinylpyrrolidone is about 33,000; and the concentration of the dilute solution of polyvinylpyrrolidone is from about 0.5% to about 4.0%, weight by volume.

8. The method of claim 1, 2 or 3 for the detection of human chorionic gonadotropin wherein said membrane has a molecular weight cut-off from about 15,000 to about 35,000; the average molecular weight of said polyvinylpyrrolidone is about 33,000; and the concentration of the dilute solution of polyvinylpyrrolidone is from about 1.0% to about 2.0%, weight by volume.

9. The method of claim 4 suitable for the detection of human chorionic gonadotropin of pregnancy or cancer in urine at a concentration as low as about 40 m.I.U./ml of urine and capable of detecting pregnancy as early as day 26 of a regular 28 day menstrual cycle wherein said membrane has a molecular weight cut-off from about 15,000 to about 35,000; the average molecular weight of said polyvinylpyrrolidone is from about 28,000 to about 35,000; and the concentration of polyvinylpyrrolidone in the urine is from about 0.1% to about 1.0%, weight by volume.

10. The method of claim 4 for the detection of human chorionic gonadotropin wherein said membrane has a molecular weight cut-off from about 15,000 to about 35,000; the average molecular weight of said polyvinylpyrrolidone is about 33,000; and the concentration of the polyvinylpyrrolidone in the urine is from about 0.1% to about 1.0%, weight by volume.

11. The method of claim 1, 2 or 3 suitable for the detection of luteinizing hormone, follicle stimulating hormone or human menopausal gonadotropin in urine wherein said membrane has a molecular weight cut-off from about 10,000 to about 35,000; the average molecular weight of said polyvinylpyrrolidone is from about 28,000 to about 35,000; and the concentration of the dilute solution of polyvinylpyrrolidone is from about 0.5% to about 4.0%, weight by volume.

12. The method of claim 1, 2 or 3 suitable for the detection of luteinizing hormone, follicle stimulating hormone or human menopausal gonadotropin in urine wherein said membrane has a molecular weight cut-off from about 10,000 to about 35,000; the average molecular weight of said polyvinylpyrrolidone is from about 28,000 to about 35,000; and the concentration of the dilute solution of polyvinylpyrrolidone is from about 1.0% to about 2.0%, weight by volume.

13. The method of claim 1, 2 or 3 suitable for the detection of luteinizing hormone, follicle stimulating hormone or human menopausal gonadotropin in urine wherein said membrane has a molecular weight cut-off from about 10,000 to about 35,000; the average molecular weight of said polyvinylpyrrolidone is about 33,000; and the concentration of the dilute solution of polyvinylpyrrolidone is from about 0.5% to about 4.0%, weight by volume.

14. The method of claim 1, 2 or 3 suitable for the detection of luteinizing hormone, follicle stimulating hormone or human menopausal gonadotropin in urine wherein said membrane has a molecular weight cut-off from about 10,000 to about 35,000; the average molecular weight of said polyvinylpyrrolidone is about 33,000; and the concentration of the dilute solution of polyvinylpyrrolidone is from about 1.0% to about 2.0%, weight by volume.

15. The method of claim 4 suitable for the detection of luteinizing hormone, follicle stimulating hormone or human monopausal gonadotropin in urine wherein said membrane has a molecular weight cut-off from about 10,000 to about 35,000; the average molecular weight of said polyvinylpyrrolidone is from about 28,000 to about 35,000; and the concentration of polyvinylpyrrolidone in the urine is from about 0.1% to aobut 1.0%, weight by volume.

16. The method of claim 4 suitable for the detection of luteinizing hormone, follicle stimulating hormone or human menopausal gonadotropin in urine wherein said membrane has a molecular weight cut-off from about 10,000 to about 35,000; the average molecular weight of said polyvinylpyrrolidone is about 33,000; and the concentration of polyvinylpyrrolidone in the urine is from about 0.1% to about 1.0%, weight by volume.

17. The method of claim 1, 2, 3 or 4 suitable for the detection of physiological conditions characterized by the presence of a polypeptide or glycoprotein antigen selected from chorionic gonadotropin, pregnant mare's serum gonadotropin, carcino embryonic antigen, luteinizing hormone, follicle stimulating hormone, human menopausal gonadotropin and thyroid stimulating hormone in urine wherein said immunologic reagent comprises:

(1) pyruvic aldehyde stabilized erythrocytes sensitized with a polypeptide or glycoprotein antigen selected from chorionic gonadotropin, human chorionic gonadotropin, pregnant mare's serum gonadotropin, carcino embryonic antigen, luteinizing hormone, follicle stimulating hormone, human menopausal gonadotropin and thyroid stimulating hormone, said stabilized erythrocytes being coupled to said antigen with a bifunctional molecule selected from glutaraldehyde, glyoxal, succinialdehyde, hexamethylene diisocyanate, toluene 2,4-diisocyanate, diethyl malonimidate dihydrochloride, dimethyl suberimidate, bis diazotized benzidine, cyanuric chloride, tetrazotized o-anisidine, and 1-ethyl-3-(3-dimethylaminopropyl)carbodiimide; and (2) an antiserum to detect said polypeptide or glycoprotein antigen.

18. The test method of claim 1, 2 3 or 4 suitable for the detection of physiological conditions characterized by the presence of a polypeptide of glycoprotein antigen selected from chorionic gonadotropin, pregnant mare's serum gonadotropin, carcino embryonic antigen, luteinizing hormone, follicle stimulating hormone, human menopausal gonadotropin and thyroid stimulating hormone in urine wherein said membrane has a molecular weight cut-off from about 10,000 is about 35,000; the average molecular weight of said polyvinylpyrrolidone is from about 28,000 to about 35,000; and the immunologic reagent comprises:

(1) pyruvic aldehyde stabilized erythrocytes sensitized with a polypeptide or glycoprotein antigen selected from chorionic gonadotropin, human chorionic gonadotropin, pregnant mare's serum gonadotropin, carcino embryonic antigen, luteinizing hormone, follicle stimulating hormone, human menopausal gonadotropin and thyroid stimulating hormone, said stabilized erythrocytes being coupled to said antigen with a bifunctional molecule selected from glutaraldehyde, glyoxal, succinialdehyde, hexamethylene diisocyanate, toluene 2,4-diisocyanate, diethyl malonimidate dihydrochloride, dimethyl suberimidate, bis diazotized benzidine, cyanuric chloride, tetrazotized o-anisidine, and 1-ethyl-3-(33-dimethylaminopropyl)carbodiimide; and (2) an antiserum to detect said polypeptide or glycoprotein antigen.

19. The method of claim 1, 2 or 3 suitable for the detection of luteinizing hormone, follicle stimulating hormone or human menopausal gonadotropin in urine wherein said membrane has a molecular weight cut-off from about 10,000 to about 35,000; the average molecular weight of said polyvinylpyrrolidone is from about 28,000 to about 35,000; the concentration of the dilute solution of polyvinylpyrrolidone is from about 1.0% to about 2.0%, weight by volume; and the immunologic reagents comprises:

(1) pyruvic aldehyde stabilized erythrocytes sensitized with a polypeptide or glycoprotein antigen selected from human chorionic gonadotropin, luteinizing hormone, follicle stimulating hormone, and human menopausal gonadotropin, said stabilized erythrocytes being coupled to said antigen with a bifunctional molecule selected from glutaraldehyde, glyoxal, succinialdehyde, hexamethylene diisocyanate, toluene 2,4-diisocyanate, diethyl malonimidate dihydrochloride, dimethyl suberimidate, bis diazotized benzidine, cyanuric chloride, tetrazotized o-anisidine, and 1-ethyl-3-(3-dimethylaminopropyl)carbodiimide; and (2) an antiserum to detect said polypeptide or glycoprotein antigen.

20. The method of claim 4 suitable for the detection of luteinizing hormone, follicle stimulating hormone or human menopausal gonadotropin in urine wherein said membrane has a molecular weight cut-off from about 10,000 to about 35,000; the average molecular weight of said polyvinylpyrrolidone is from about 28,000 to about 35,000; the concentration of polyvinylpyrrolidone in the urine is from about 0.1% to about 1.0%, weight by volume; and the immunologic reagent comprises:

(1) pyruvic aldehyde stabilized erythrocytes sensitized with a polypeptide or glycoprotein antigen selected from human chorionic gonadotropin, luteinizing hormone, follicle stimulating hormone, and human menopausal gonadotropin, said stabilized erythrocytes being coupled to said antigen with a bifunctional molecule selected from glutaraldehyde, glyoxal, succinialdehyde, hexamethylene diisocyanate, toluene 2,4-diisocyanate, diethyl malonimidate dihydrochloride, dimethyl suberimidate, bis diazotized benzidine, cyanuric chloride, tetrazotized o-anisidine, and 1-ethyl-3-(3-dimethylaminopropyl)carbodiimide; and (2) an antiserum to detect said polypeptide or glycoprotein antigen.

* * * * *

UNITED STATES PATENT AND TRADEMARK OFFICE
CERTIFICATE OF CORRECTION

PATENT NO. : 4,208,187
DATED : June 17, 1980
INVENTOR(S) : Morris L. Givner

It is certified that error appears in the above-identified patent and that said Letters Patent are hereby corrected as shown below:

Column 4, line 64, "secific" should read —specific—.

Column 5, line 2, after "gonadotropin" insert —antiserum—.

Column 9, line 13, "Secondarly" should read —Secondly—.

Claim 15, line 3, "monopausal" should read —menopausal—.

Claim 15, line 8, "aobut" should read —about—.

Claim 18, line 19 of column 19 "33" should read —3—.

Signed and Sealed this

Twenty-ninth Day of September 1981

[SEAL]

Attest:

GERALD J. MOSSINGHOFF

Attesting Officer     Commissioner of Patents and Trademarks